United States Patent [19]

Chandler

[11] Patent Number: 5,514,537
[45] Date of Patent: May 7, 1996

[54] PROCESS AND APPARATUS FOR SORTING SPERMATOZOA

[75] Inventor: John E. Chandler, Baton Rouge, La.

[73] Assignee: Board of Supervisors of Louisiana State University and Agricultural and Mechanical College, Baton Rouge, La.

[21] Appl. No.: 347,793

[22] Filed: Nov. 28, 1994

[51] Int. Cl.$^6$ .............................. A01N 1/02; A61K 35/52
[52] U.S. Cl. .................. 435/2; 424/561; 436/906
[58] Field of Search ................. 435/2; 210/656, 210/702; 424/561; 436/63, 807, 906

[56] References Cited

U.S. PATENT DOCUMENTS

| | | | |
|---|---|---|---|
| 4,083,957 | 4/1978 | Lang | 424/78 |
| 4,191,749 | 3/1980 | Bryant | 424/105 |
| 4,339,434 | 7/1982 | Ericsson | 424/105 |
| 4,448,767 | 5/1984 | Bryant | 424/85 |
| 4,474,875 | 10/1984 | Shrimpton | 435/2 |
| 4,605,558 | 8/1986 | Shrimpton | 424/105 |
| 4,722,887 | 2/1988 | Fabricant et al. | 435/2 |
| 4,999,283 | 3/1991 | Zavos et al. | 435/2 |
| 5,021,244 | 6/1991 | Spaulding | 424/561 |

FOREIGN PATENT DOCUMENTS 9117188  11/1991  WIPO .

OTHER PUBLICATIONS

Daya S., Separation of Motile Human Spermatozoa . . . Gamete Research 17: 375–380 (1987).
Casey P., Column Separation of Motile Sperm . . . Andrology (14) 2 Mar./Apr. (1993) pp. 142–148.
K. Cui et al., "X Larger than Y," Nature, vol. 366, pp. 117–118 (Nov. 1993).
Chandler et al., "Videomicroscopic Comparison of Bull Sperm and Leukocyte Chromosome Areas as related to Gender," J. Dairy Sci., vol. 73, pp. 2129–2135 (1990).
B. L. Gledhill et al., "Identifying X– and Y–Chromosome–Bearing Sperm by DNA Content: Retrospective Perspectives and Prospective Opinions, " in R. P. Amann et al. (eds.) *Prospects for Sexing Mammalian Sperm*, pp. 177–191 (1982).
W. A. Wells et al., "Equipment, Standardization and Applications of Image Processing," Amer. J. Clin. Path., vol. 99, pp. 48–56 (1993).
D. G. Cran et al., "Production of Bovine Claves Following Separation of X– and Y–Chromosome Bearing Sperm and In Vitro Fertilisation," Veterinary Record, vol. 132, pp. 40–41 (1993).
Fike et al., "Preparative Cell Electrophoresis," Preparative Biochemistry, vol. 3, No. 2, pp. 183–193 (1973).

*Primary Examiner*—Ralph J. Gitomer
*Attorney, Agent, or Firm*—John H. Runnels

[57] ABSTRACT

A method and apparatus are disclosed for the mechanical sorting of mammalian spermatozoa by sex-type, into a fraction enriched in X-chromosome-bearing spermatozoa, and a fraction enriched in Y-chromosome-bearing spermatozoa. Because of their different DNA content, Y-chromosome spermatozoa are slightly smaller than X-chromosome spermatozoa. A column is packed with two sizes of beads. The size of the smaller beads is chosen such that, on average, Y-chromosome spermatozoa will readily fit into the interstices between the smaller beads, while X-chromosome spermatozoa, on average, will not readily fit into those interstices. The size of the larger beads is chosen such that the smaller beads will not readily fit into the interstices between the larger beads. A liquid sample containing the sperm is run through a column so that the liquid first encounters the larger beads, and then encounters the smaller beads. The beads act as a sieve, creating a fraction in the larger beads enriched in X-chromosome spermatozoa, and a fraction in the smaller beads enriched in Y-chromosome spermatozoa.

15 Claims, No Drawings

PROCESS AND APPARATUS FOR SORTING SPERMATOZOA

This invention pertains to the sorting of spermatozoa, particularly to the differential separation of mammalian spermatozoa by sex-type.

In mammals, the male gamete or spermatozoan controls the sex of offspring. Each spermatozoan contains either an X-type or a Y-type sex-determining chromosome. An X-chromosome spermatozoan creates female offspring after fertilization with an oocyte, while a Y-chromosome spermatozoan creates male offspring after fertilization. In some instances it is thought desirable to alter the natural distribution of X- and Y- containing spermatozoa, to differentially select for either female or male offspring. Separation techniques have been developed which take advantage of the slight, but significant, differences in physical characteristics between X- and Y-type spermatozoa.

A chromosome's size is related to its DNA content. Because an X chromosome is substantially larger than a Y chromosome, an X-chromosome-bearing sperm will be physically larger than one bearing a Y chromosome. Based on mean haploid DNA quantity, the difference in weight between X- and Y-chromosome-bearing mammalian sperm is known to be between about 2.5% and about 4.5%.

Chandler et al., "Videomicroscopic Comparison of Bull Sperm and Leukocyte Chromosome Areas as Related to Gender," J. Dairy Sci., vol. 73, pp. 2129–2135 (1990), used discriminate analysis of bovine chromosomal areas to assign normal spermatozoa head area data into two groups, based on the presence of the X or Y chromosome. The resulting spermatozoal groups had a mean head area difference of 3.2%.

Certain dyes such as ethidium bromide and acridine orange have been used to evaluate DNA content of spermatozoa. Fluorescence intensity of the dye is proportional to the amount of dye absorbed. B. L. Gledhill et al., "Identifying X- and Y-Chromosome-Bearing Sperm by DNA Content: Retrospective Perspectives and Prospective Opinions," in R. P. Amann et al. (eds.) *Prospects for Sexing Mammalian Sperm*, pp. 177–91 (1982), discloses the use of 4',6-diamidino-2-phenylindole (DAPI) staining, and epi-illumination with orienting-flow cytometry, to show that the mean DNA content of bovine spermatozoa from frozen semen exhibited two distinct, but overlapping peaks of fluorescence. These peaks were nearly equal in size, and were separated by a 3.9% difference in intensity.

W. A. Wells et al., "Equipment, Standardization and Applications of Image Processing," Amer. J. Clin. Path., vol. 99, pp. 48–56 (1993) discloses that the optical density of cell nuclei is directly proportional to the DNA content, or the ploidy, of the cell.

D. G. Cran et al., "Production of Bovine Calves Following Separation of X- and Y-Chromosome Bearing Sperm and In Vitro Fertilisation," Veterinary Record, vol. 132, pp. 40–41 (1993) discloses the use of a fluorescence activated cell sorter to separate bovine X- and Y- chromosome-bearing sperm based on differences in DNA content, in quantities adequate for in vitro fertilization, but not for artificial insemination.

Fike et al., "Preparative Cell Electrophoresis," Preparative Biochemistry, vol. 3, no. 2, pp. 183–93 (1973), discloses the separation of erythrocytes by electrophoresis through a glass bead column. This paper also discloses that the upper bound on the length of objects that can pass through the interstices of a collection of rigid packed spheres of equal size is about 15.5% of the packed sphere radius.

U.S. Pat. Nos. 4,191,749 and 4,448,767 disclose a non-mechanical, immunosorbent method for sorting sperm in which an antibody is bound to beads of diameter 80 to 120 micron.

U.S. Pat. No. 4,999,283 discloses an immunological method for separating sperm in which antibody is conjugated to agarose beads of 40–120 particle size.

U.S. Pat. No. 4,474,875 discloses a separation technique based on differential buoyancy of cooled, immobilized sperm in a density gradient. See also U.S. Pat. No. 4,605,558.

U.S. Pat. No. 4,083,957 discloses a sperm separation method based on electrostatic interaction with a poly-electrostatic, charged material such as an ion exchange resin. This patent teaches that size differences between X-type and Y-type spermatozoa are insufficient to permit good separation by simple filtration within a short enough time to be practical.

U.S. Pat. No. 5,021,244 discloses an antibody-based method for sorting sperm, as well as a method based on flow cytometry.

U.S. Pat. No. 4,722,887 discloses a sperm separation method using partition chromatography, based on differential expression of a sulfoglycolipid.

It has not previously been thought that spermatozoa could be sorted by sex-type through mechanical means alone. Mechanical separation has not been thought to be capable of achieving a fine enough resolution to separate groups of cells with mean size differences on the order of 3% to 10%.

A novel and unexpected method and apparatus have been discovered for efficiently sorting spermatozoa by mechanical means. The sorted cells remain viable after separation. Rigid packed spheres, such as glass spheres, of at least two different sizes are used to create a type of sieve. In the presence of a pressure gradient across the packed spheres, the cells are sorted through the interstices of the spheres based on their sizes. The slightly larger X-type spermatozoa may thus be separated from the slightly smaller Y-type spermatozoa. Preferably two different sizes of glass beads are used. The sizes of the beads depends on sperm sizes for the species in question. For example, it has been found that bovine spermatozoa may be sorted with glass beads having diameters of about 100 microns and about 22 microns.

More generally, the respective sphere diameters may be selected by taking the smaller bead radius such that a distance equal to about 15.5% of that radius lies between the respective mean diameters of the cells to be segregated. The larger sphere diameter is preferably selected so that the smaller spheres do not fit within the interstices between the larger spheres, giving an upper bound for the radius of the larger spheres of about $(0.155)^{-1}=6.46$ times the radius of the smaller spheres. Typically, the larger beads would be somewhat smaller than this upper limit, but would still have a radius large enough to permit both types of spermatozoa to fit between the interstices. The larger beads act to align the sperm cells prior to entering the interstices of the smaller beads, and to keep the smaller beads from clogging.

An applied hydrostatic force may be used to speed the sieving process. Preferably, a vacuum is applied to one end of a cylinder made of a flexible material of high tensile strength, although the same result should also be obtainable by using positive pressure to force the mixture through the sieve. This cylinder has two, and preferably three main regions. The input end contains a length of the larger spheres, preferably glass beads, tightly packed. The center region contains a length of the smaller spheres, again preferably glass beads, tightly packed, immediately adjacent to the input end. This center region is preferably about equal in length to the input end region. Finally, the optional but preferred buffer output end region contains a length of the larger spheres, a length that may be as long as, or shorter than, the other two regions. More generally, this optional but preferred buffer end region contains a plurality of tightly packed third beads, wherein said third beads are substantially spherical and substantially uniform in radius, wherein the third bead radius is greater than the radius of the beads in the center region and is less than 6.46 times the radius of those center-region beads.

A sample of cells, preferably a diluted sample of cells, is inserted into the input end of the cylinder, and the vacuum or other pressure means is activated, preferably exerting a pressure differential of about 500 mm Hg across the cylinder. The sample progresses through the input end region until it reaches the border between the input and center regions. Separation occurs as the smaller cells, typically the Y-chromosome spermatozoa, are taken through the interstices of the smaller spheres by the force of the vacuum or other pressure means, leaving the larger cells, typically the X-chromosome spermatozoa, behind in the region of the larger spheres. After complete evacuation of the sample, over a time readily determined for a particular sample type, depending on viscosity and other characteristics of the sample, the vacuum or other pressure means is deactivated. The input end region and the center region are separated from each other and from the buffer output end region of the cylinder, preferably with a surgeon's scalpel, leaving two sphere-filled segments of the cylinder enriched in X-chromosome spermatozoa and Y-chromosome spermatozoa, respectively. The spermatozoa are then collected from the packed sphere media, and the spheres may optionally be washed and recycled for further separations.

EXAMPLE 1

A separatory sieve (sometimes referred to as a "SEPDEVICE") was prepared with a French straw (13.4 cm×0.22 cm diameter, total volume approximately 0.5 ml) (I.M.V. International Corp, Minneapolis, Minn.) packed with 100 micron and 22 micron diameter glass beads. The 100 micron glass beads were obtained from VWR Scientific, Houston, Tex., and the 22 micron glass beads were obtained from Duke Scientific Corporation, Palo Alto, Calif. The input end of the straw had a 5.08 cm length packed with the 100 micron beads. The center region of the straw had a 5.08 cm length packed with 22 micron beads, and the buffer output end region had a 3.04 cm length packed with 100 micron beads. Both ends of the column were covered with a 5 micron nylon mesh to maintain the integrity of the column. A vacuum source (with a trap) was connected to the buffer output end of the column.

EXAMPLE 2

Three straws containing 0.5 ml frozen bovine semen were thawed (40° C., 20 sec) and diluted with 3 ml of 2.9% sodium citrate buffer. Four ml of diluted semen were suctioned into the 5.08 cm-long section of 100 micron beads in the column of Example 1, under a vacuum of 500 mm Hg until completion. An additional 5 ml of buffer was suctioned into the column to insure adequate separation. Upon complete evacuation of the buffer after 22 minutes, the straw was cut with a scalpel at the interfaces between the 100 micron bead sections and the 22 micron bead section. Each section was placed into 4 ml of citrate buffer and gently agitated to wash the beads and sperm out of the column.

The beads were allowed to settle out by gravity for about 2 min. The sperm and supernatant were removed, and the glass beads were washed in 1N HCl before reuse. Hemocytometer counts were made on a 1:80 dilution of the supernatant from each section, as well as on fluids captured in the vacuum trap.

The separated samples were resuspended to original volume in buffer, and were evaluated for motility by phase microscopy, and for concentration by hemocytometer count. The separated samples were then fixed with 0.2% glutaraldehyde for subsequent acrosomal integrity evaluation.

Video intensified fluorescence microscopy (VIFM) was used in analysis, because VIFM has been shown to be more accurate in identifying various neoplasms than is flow cytometry. The higher accuracy results because the integrity of the biological specimen can be evaluated simultaneously with the intensity of the fluorescent dye. Image analysis coupled with video enhanced contrast microscopy (VECM) and VIFM microscopy are sensitive tools for measuring various cellular features and functions.

Spermatozoa head area and fluorescence intensity were evaluated with a research microscope with differential interference contrast optics (Carl Zeiss, Inc., Thornwood, N.Y.). Fixed samples were stained with Hoechst 33258 (Sigma Chemical Co., St. Louis, MO.) and evaluated for head area and fluorescence intensity via image analysis. A video camera was attached to the phototube and interfaced to an expanded memory Step 386™ computer (Everex, Inc., Fremont, Calif.) using a Targa M-8™ video board (AT&T, Indianapolis, Ind.). The video system used a silicon intensifier target camera (Hamamatsu, Advanced Instruments Inc., New Orleans, La.) with greater than 500 lines and less than $10^{-4}$ lux resolution and a flat screen monitor (Sony Triniton™, Meyer Instruments, Houston, Tex.). The monitor resolution was 512×400 pixels, with 256 grey intensity shades per pixel. The image analysis equipment and microscope were calibrated using a micrometer (Carl Zeiss Inc.). The imaging system produced a total magnification of 4150× on the face of the monitor, which yielded (84 pixels)$^2$ per square micron. Head area measurements were made by tracing the edge of the spermatozoan head. This tracing also set the area of interest from a captured picture viewed through differential interference contrast optics. Gray intensity was determined from the area of interest of the captured image of Hoechst 33258-stained spermatozoa at constant white light illumination ($FI_t$). The cells were simultaneously exposed to transmitted white light and reflected UV light using a 50 W mercury arc lamp. The UV light was passed through a FITC filter set (exciter BP 365, dichromatic beam spitter FT 395, barrier LP 420). The "double-exposed" image was captured, and absolute grey intensity ($FI_{both}$) was collected Corrected fluorescent intensity ($FI_c$) was calculated as $FI_c = FI_{both} - FI_t$.

There was a 5.09% difference ($P<0.05$) between mean sperm head areas of the separated samples, with the head area of spermatozoa captured in the small bead section of the SEPDEVICE being smaller. There was a 3.19% difference ($P<0.05$) between mean sperm fluorescent intensity of separated samples, with the spermatozoa captured in the large bead section of the SEPDEVICE having a greater intensity. The number of spermatozoa captured in both sections of the SEPDEVICE was nearly the same (Table 1). Motility was reduced from initial motility in both separated samples. The separation process had a greater effect on the acrosomal integrity of the large bead sperm than those retained in the small beads (Table 1).

TABLE 1

|  | Hemocytometer count (x $10^6$) | Motility % | % Intact Acrosomes |
|---|---|---|---|
| LARGE BEAD SPERM | 1.8 | >5 | 18 |
| SMALL BEAD SPERM | 4.0 | >5 | 51 |
| CONTROL SPERM[1] | 14.0 | — | 78 |

[1]Sampled before application to the SEPDEVICE.

EXAMPLE 3

The experiment of example 2 was repeated, using a different frozen ejaculate from the same bull. Separation was completed in 71 minutes. The time varied due to differing times to complete evacuation of the sample.)

There was a 7.92% difference (P<0.05) between mean sperm head areas of separated samples, with head area of spermatozoa captured in the small bead section of the SEPDEVICE being smaller. There was a 7.65 % difference (P<0.05) between mean sperm fluorescent intensity of the separated samples, with the spermatozoa captured in the large bead section of the SEPDEVICE having a greater intensity. The number of spermatozoa captured in both sections of the SEPDEVICE was the same (Table 2). Motility was severely reduced from normal in both separated samples. The separation process had a greater effect on the acrosomal integrity of the large bead sperm than those retained in the small bead section.

TABLE 2

|  | Hemocytometer count (x $10^6$) | Motility % | % Intact Acrosomes |
|---|---|---|---|
| LARGE BEAD SPERM | 6.75 ± 3.5 | 0 | 23 |
| SMALL BEAD SPERM | 6.75 ± 3.5 | 0 | 44 |
| CONTROL SPERM[1] | 13.5 ± 5.6 | — | 78 |

[1]Sampled before application to the SEPDEVICE.

EXAMPLE 4

The experiment of Example 2 was repeated, but using 22 micron washed beads from the previous experiments, and using semen from a different bull. Separation was completed in 90 minutes.

There was a 5.03% difference (P<0.05) between mean sperm head areas of separated samples, with head area of spermatozoa captured in the small bead section of the SEPDEVICE being smaller. There was a 9.78% difference (P<0.05) between mean sperm fluorescent intensity of the separated samples, with the spermatozoa captured in the large bead section of the SEPDEVICE having a greater intensity. The number of spermatozoa captured in both sections of the SEPDEVICE was nearly the same (Table 3). Motility was reduced from normal in both separated samples. The separation process had a greater effect on the acrosomal integrity of the large bead sperm than those retained in the small beads (Table 3).

TABLE 3

|  | Hemocytometer count (x $10^6$) | Motility % | % Intact Acrosomes |
|---|---|---|---|
| LARGE BEAD SPERM | 11.9 ± 3.7 | >5 | 54 |
| SMALL BEAD SPERM | 10.0 ± 3.8 | >5 | 65 |
| CONTROL SPERM[1] | 37.5 ± 4.3 | — | 78 |

[1]Sampled before application to the SEPDEVICE.

EXAMPLE 5

The experiment of Example 2 was repeated, but with semen from a different bull, and using recycled small beads. Separation was complete in 130 minutes.

There was a 2.62% difference (P>0.05) between mean sperm head areas of separated samples, with head area of spermatozoa captured in the small bead section of the SEPDEVICE being smaller. There was a 0.02% difference (P>0.05) between mean sperm fluorescent intensity of the separated samples, with the spermatozoa captured in the large bead section of the SEPDEVICE having a slightly greater intensity. The number of spermatozoa captured in the two sections of the SEPDEVICE differed considerably (Table 4). Motility was reduced from normal in both separated samples; however, the sperm retained in the small beads were less affected. The separation process caused a reduction in intact acrosomes for both bead classes, with those in the large bead section being affected slightly more (Table 4).

TABLE 4

|  | Hemocytometer count (x $10^6$) | Motility % | % Intact Acrosomes |
|---|---|---|---|
| LARGE BEAD SPERM | 12.8 ± 9.0 | >5 | 32 |
| SMALL BEAD SPERM | 6.4 ± 9.0 | 19 | 37 |
| CONTROL SPERM[1] | 32.5 ± 12.6 | 55 | 50 |

[1]Sampled before application to the SEPDEVICE.

EXAMPLE 6

The experiment of Example 2 was repeated, but with diluted, unfrozen semen from a new bull. Separation was complete in 70 minutes.

There was a 4.22% difference (P<0.05) between mean sperm head areas of separated samples, with head area of spermatozoa captured in the small bead section of the SEPDEVICE being smaller. There was a −14.92% difference (P<0.05) between mean sperm fluorescent intensity of the separated samples, with the spermatozoa captured in the small bead section of the SEPDEVICE having a greater intensity. The number of spermatozoa captured in both sections of the SEPDEVICE differed considerably (Table 5). Motility was reduced from normal in both separated samples. However, the sperm retained in the small beads were more affected. The separation process caused a reduction in percent intact acrosomes for both sections, with those in the LARGE BEAD section being affected more (Table 5).

TABLE 5

|  | Hemocytometer count (× 10⁶) | Motility % | % Intact Acrosomes |
|---|---|---|---|
| LARGE BEAD SPERM | 17.5 | 15 | 17 |
| SMALL BEAD SPERM | 7.5 | 0 | 23 |
| CONTROL SPERM[1] | 30.0 | 60 | 73 |

[1]Sampled before application to the SEPDEVICE.

EXAMPLE 7

Bovine sperm stained with Hoechst 33342, already separated by sex type via flow cytometry, were obtained from Dr. David Cran, Cambridge, England. Sperm were fixed in PBS-formalin for shipping, then washed and resuspended in 0.2% glutaraldehyde. Samples were coded to hide sex identification of the samples during image analysis of both area and fluorescence intensity. Data were analyzed using a simple "t" test to evaluate differences between means. Percent differences in spermatozoal head area or fluorescence intensity were expressed as small bead section to large bead section ratio, as: %difference=(1—(SMALL BEAD/LARGE BEAD))×100%.

There was a 1.2% difference ($P<0.05$) between mean sperm head areas of flow cytometer-sorted samples, with the head area of the Y-chromosome spermatozoa being smaller. There was a 1.79% difference ($P<0.05$) between mean sperm fluorescent intensity of the flow cytometer-sorted spermatozoa, with the X-chromosome sperm having greater intensity. The percent intact acrosomes for Y-bearing sperm was slightly greater than that for X-bearing sperm (Table 6).

TABLE 6

|  | Primary Abnormalities % | Secondary Abnormalities % | Intact Acrosomes % |
|---|---|---|---|
| X BEARING | 15 | 28 | 52 |
| Y BEARING | 25 | 21 | 57 |

The cytometer-sorted samples served as controls for assessing the head area and head fluorescence intensity results obtained from the other Examples. All Examples but Example 5 yielded populations of spermatozoa with head area differences of the magnitude and direction that would be expected if separation by sex chromosome had been achieved. Example 5 head area differences were in the right direction numerically, but were not statistically significant. All examples except Examples 5 and 6 showed head fluorescence intensities in the magnitude and direction that would be expected if separation by sex chromosome had been achieved. Example 5 fluorescence intensity data showed statistically insignificant differences. Example 6 fluorescence intensity showed fluorescence intensity differences in the reverse direction to what would be expected. The reason for this apparent discrepancy is currently unknown. Therefore, with one unexplained discrepancy, comparison of head area and head fluorescence intensity of the trials with that of the sex-separated controls showed that the separation apparatus effectively sorted the bovine spermatozoa by sex.

EXAMPLE 8

The separations were validated by a semi-quantitative PCR analysis, using a pair of primers specific for a 194-base-pair region on the bovine Y-chromosome. The 194-base-pair segment was amplified using primers BRY1A and BRY1B, chosen by analysis with the PC Gene™ program of a bovine Y-chromosome-specific DNA sequence reported in Australian National University international (PCT) patent application no. WO 88/01300, filed Aug. 11, 1987. The two primers were selected to optimize the length of the segment amplified (194 base pairs) and the calculated annealing temperature of the DNA duplex (58° C.).

The two primer sequences used were the following:

BRY1A (SEQ ID NO. 1)CCAATACACAGAGGTCATG-GTGGG

BRY1B (SEQ ID NO. 2)GGAAGACTATGCAGGTAG-CAGGTGC

Separated samples were obtained by repeating the experiment of Example 2, but with diluted, unfrozen semen from a new bull. Blood from the same bull supplying the semen sample served as a positive control for the presence of the Y chromosome. Blood from a randomly selected cow served as a negative control.

The separated spermatozoa and the blood samples were separately treated to release DNA with a lysis solution containing 200 mM KOH and 50 mM DTT (dithiothreitol), incubated at 65° C. for 20 minutes. Each sample was standardized to have a constant number of nucleated cells, so that all samples contained approximately equal numbers of nuclei. In particular, a hemocytometer was used to count 500,000 white blood cells or 500,000 spermatozoa in each sample, as appropriate. Following incubation, a neutralizing solution was added to the samples (900 mM Tris-HCl, 300 mM KCl, 200 mM HCl. The samples were then placed in a Perkin-Elmer thermal cycler, along with primers BRY1A and BRY1B, and standard PCR reagents according to the manufacturer's instructions. The DNA was amplified for 35 cycles, and then electrophoresed on a 3% ethidium bromide-stained agarose gel. The 194-bp band fluoresced under excitation from a 302 nm light, and the fluorescence image was recorded on Polaroid® Type 667 panchromatic black-and-white film, without a filter. The photographic image was then digitized with a silicon-intensified camera interfaced to a computer. The digitized image was evaluated by measuring the average intensity of 200 columns of 12 pixels each in the center of each band. The measured intensities are given in Table 7.

Two different buffer systems for the PCR amplification of sperm-derived DNA were evaluated, both from the Invitrogen Corp. (San Diego, Calif.) PCR Optimizer Kit. The "F buffer" was pH 9.0, with a $Mg^{++}$ concentration of 2.0 raM. The "N buffer" was pH 10.0, with a $Mg^{++}$ concentration of 2.0 raM. As discussed further below, the F buffer was preferred for sperm samples, as the N buffer gave unsatisfactory results.

A single buffer, the Invitrogen "M buffer," was used for the blood samples. The "M buffer" was pH 10.0, with a $Mg^{++}$ concentration of 1.5 mM. Different buffers were used for the blood and sperm samples, as it is well-known that optimal buffers for PCR amplifications differ according to the type of biological sample involved. The "M buffer" appeared to give good results for the blood samples.

TABLE 7

| Sample | Fluorescence Intensity | Chi-Squared Value, versus Cow Blood | Chi-Squared Value, versus Bull Blood | Chi-Squared Value, versus Small Bead Sperm for the Same Buffer System |
|---|---|---|---|---|
| Large Bead Sperm (F buffer) | 130.24 | 69.67[a] | 0.33 | 3.15[b] |
| Small Bead Sperm (F buffer) | 150.47 | 118.42[a] | 1.32[c] | — |
| Large Bead Sperm (N buffer) | 70.88 | 0.82 | 31.91[a] | 0.25 |
| Small Bead Sperm (N buffer) | 75.24 | 2.11[c] | 27.84[a] | — |
| Bull Blood | 137.00 | 84.52[a] | — | — |
| Cow Blood | 63.65 | — | 39.27[a] | — |
| Background | 54.73 | 1.45[#] | — | — |

Notes to Table 7: Superscript letters indicate a statistical difference between an observed value and the comparison value for that column; in particular, "a" denotes a statistical difference from the comparison value at $P<0.01$; "b" denotes a statistical difference from the comparison value at $P<0.1$, and "c" denotes a numerical difference from the comparison value at $P<0.25$. In the bottom row of Table 7, the "#" superscript denotes that background was used as the expected value, and cow blood was used as the observed value, rather than vice versa.

The results for the N buffer system, especially when compared to the results for the F buffer system, showed that the N buffer was less than optimal for the semi-quantitative PCR measurements. By contrast, the F buffer gave good results.

Cow blood served as a negative control, as a check for such things as stray DNA contamination of the buffers or the water, and the specificity of the PCR primers. There was a significant difference for comparisons between cow blood and bull blood, and for the comparisons of both large and small bead F buffer systems to cow blood.

Bull blood served as a positive control for the presence of the Y chromosome. The bands for both separated sperm samples with the F buffer system had intensities numerically similar to that for bull blood, and statistically different from that for cow blood. The intensity of the large bead sample in the F buffer system was less than the intensity for bull blood, suggesting a partial depletion of Y chromosomes for that sample, although the difference was not statistically significant. The fluorescence intensity of the small bead sample in the F buffer system was greater than that for the bull blood, suggesting an enrichment of Y chromosome in that sample, at $P<0.25$.

With the F-buffer system, the fluorescence intensity in the small bead sample was 15.5% greater than that for the large bead sample, $P<0.1$. The intensities of the two samples would be expected to be the same had no separation occurred.

The separations will also be validated by karyotyping oocytes microinjected with separated sperm, by karyotyping embryos produced through artificial insemination with the separated sperm, and by observing sex ratios of offspring bred with separated sperm.

Although the examples described above all used bovine semen, the same principles will work to sort spermatozoa from other mammalian species. For example, the methods and apparatus of the present invention may be used to sort sperm by sex type in cattle, horses, sheep, pigs, and other mammalian species of interest. Using the geometric relationships described above for the relative sizes of the beads and the sperm cells being sorted, appropriate bead sizes for sorting sperm from a particular species may readily be chosen. The size of the small beads should be such that the length of the interstices between packed beads, 15.5% of the bead radius, is between the mean sizes of X-type and Y-type sperm for the species, preferably about halfway between those two means. The size of the large beads should be larger than that of the small beads, and is preferably such that the small beads do not fit within the interstices between the large beads; i.e., the radius of the large beads should preferably be somewhat less than 6.46 times the radius of the small beads. The beads are preferably approximately spherical, to promote uniformly sized interstices. Vibration helps in obtaining a tight packing of the beads. Routine variation of the viscosity and the pressure gradient can readily be used to optimize the separation protocol for a given species.

The entire disclosures of all references cited in the specification are hereby incorporated by reference in their entirety. In the event of an otherwise irresolvable conflict, however, the present specification shall control.

I claim:

1. An apparatus for sorting sperm from a mammalian species into a first fraction enriched in sperm bearing an X chromosome and a second fraction enriched in sperm bearing a Y chromosome, said apparatus comprising a column, a plurality of first beads, and a plurality of second beads, wherein:
  (a) said first beads are tightly packed in a first region of said column;
  (b) said second beads are tightly packed in a second region of said column;
  (c) said first and second regions are distinct regions within said column, said first and second regions being adjacent to one another;
  (d) said second beads are substantially spherical, and are substantially uniform in radius, wherein the second beads have a radius such that a length equal to 0.155 times the second bead radius is intermediate in magnitude between the mean radius of the mammalian species' sperm containing an X chromosome, and the mean radius of the mammalian species' sperm containing a Y chromosome; and
  (e) said first beads are substantially spherical, and are substantially uniform in radius, wherein the first beads have a radius greater than the second bead radius.

2. An apparatus as recited in claim 1, additionally comprising a source for creating a pressure gradient across said column, wherein the pressure decreases in a direction from the first region to the second region.

3. An apparatus as recited in claim 1, additionally comprising a plurality of third beads, wherein said third beads are substantially spherical and substantially uniform in radius, wherein the third beads have a radius greater than the second bead radius and less than 6.46 times the second bead radius, and wherein said third beads are tightly packed in a third region of said column, wherein said third region is distinct from said first and second regions, and wherein said second region lies intermediate and adjacent to each of said first and third regions.

4. An apparatus as recited in claim 3, wherein the radius of the first beads and of the third beads is approximately 100 microns, and wherein the radius of the second beads is approximately 22 microns.

5. An apparatus as recited in claim 3, wherein said first beads, said second beads, and said third beads each comprise glass beads.

6. A method for sorting sperm from a mammalian species into a first fraction enriched in sperm bearing an X chromosome and a second fraction enriched in sperm bearing a Y chromosome, said method comprising the steps of:
  (a) placing a liquid containing the sperm into a first region of a sorting apparatus comprising a column, a plurality of first beads, and a plurality of second beads, wherein:
    (i) said first beads are tightly packed in a first region of said column;
    (i) said second beads are tightly packed in a second region of said column;
    (iii) said first and second regions are distinct regions within said column, said first and second regions being adjacent to one another;
    (iv) said second beads are substantially spherical, and are substantially uniform in radius, wherein the second beads have a radius such that a length equal to 0.155 times the second bead radius is intermediate in magnitude between the mean radius of the mammalian species' sperm containing an X chromosome, and the mean radius of the mammalian species' sperm containing a Y chromosome; and
    (v) said first beads are substantially spherical, and are substantially uniform in radius, wherein the first bead radius is greater than the second bead radius; and
  (b) causing the liquid to flow in a direction from the first region through the second region, until that fraction of the liquid within said first beads is enriched in sperm bearing an X chromosome and that fraction of the liquid within said second beads is enriched in sperm bearing a Y chromosome.

7. A method as recited in claim 6, wherein the sperm are bovine sperm.

8. A method as recited in claim 6, wherein the sperm are equine sperm.

9. A method as recited in claim 6, wherein the sperm are ovine sperm.

10. A method as recited in claim 6, wherein the sperm are porcine sperm.

11. A method as recited in claim 6, wherein said sorting apparatus additionally comprises a source for creating a pressure gradient across said column, wherein the pressure decreases in a direction from the first region to the second region; and wherein the liquid flows under the pressure gradient in a direction from the first region through the second region.

12. A method as recited in claim 6, wherein said sorting apparatus additionally comprises a plurality of third beads, wherein said third beads are substantially spherical and substantially uniform in radius, wherein the third beads have a radius greater than the second bead radius and less than 6.46 times the second bead radius, and wherein said third beads are tightly packed in a third region of said column, wherein said third region is distinct from said first and second regions, and wherein said second region lies intermediate and adjacent to each of said first and third regions; and wherein the liquid is caused to flow in a direction from the first region through the second region and through the third region, until that fraction of the liquid within said first beads in the first region is enriched in sperm bearing an X chromosome and that fraction of the liquid within said second beads, within said third beads, or within both said second beads and said third beads is enriched in sperm bearing a Y chromosome.

13. A method as recited in claim 12, wherein said first beads, said second beads, and said third beads each comprise glass beads.

14. A method as recited in claim 12, wherein the radius of the first beads and of the third beads is approximately 100 microns, and wherein the radius of the second beads is approximately 22 microns.

15. A method as recited in claim 14, wherein the sperm are bovine sperm.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

CCAATACACA GAGGTCATGG TGGG    24

( 2 ) INFORMATION FOR SEQ ID NO:2:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:2:

GGAAGACTAT GCAGGTAGCA GGTGC    25